United States Patent [19]

Vaillancourt

[11] Patent Number: 4,645,495
[45] Date of Patent: Feb. 24, 1987

[54] VASCULAR ACCESS IMPLANT NEEDLE PATCH

[76] Inventor: Vincent L. Vaillancourt, 14 Bunyan Dr., Livingston, N.J. 07039

[21] Appl. No.: 748,993

[22] Filed: Jun. 26, 1985

[51] Int. Cl.⁴ .............................................. A61M 5/00
[52] U.S. Cl. .................................... 604/180; 604/117; 604/177; 604/306
[58] Field of Search ........ 604/180, 117, 175, 177–179, 604/306; 128/DIG. 26

[56] References Cited

U.S. PATENT DOCUMENTS

| | | | |
|---|---|---|---|
| 2,714,382 | 8/1955 | Alcala | 604/306 |
| 3,683,911 | 8/1972 | McCormick | 604/180 |
| 3,870,043 | 3/1975 | Dunn | 604/272 |
| 4,235,234 | 11/1980 | Whitney et al. | 604/177 X |
| 4,353,367 | 10/1982 | Hunter et al. | 604/905 X |
| 4,380,234 | 4/1983 | Kamen | 604/180 |
| 4,464,178 | 8/1984 | Dalton | 604/180 |
| 4,534,762 | 8/1985 | Heyer | 604/180 |

*Primary Examiner*—Stephen C. Pellegrino
*Attorney, Agent, or Firm*—Kenyon & Kenyon

[57] ABSTRACT

The needle patch has a Huber needle which is encased between a pair of flexible transparent discs. The needle has a depending angled portion which extends through an aperture in the lower disc for insertion in an implanted vascular access device. The lower disc also has an adhesive layer for securement to the skin about the injection site while the upper disc has a projection defining a reservoir above the aperture of the lower disc for dispensing of an antiseptic ointment to the injection site. A rigid housing is integrally formed with the discs to provide a finger gripping portion for insertion of the needle.

21 Claims, 10 Drawing Figures

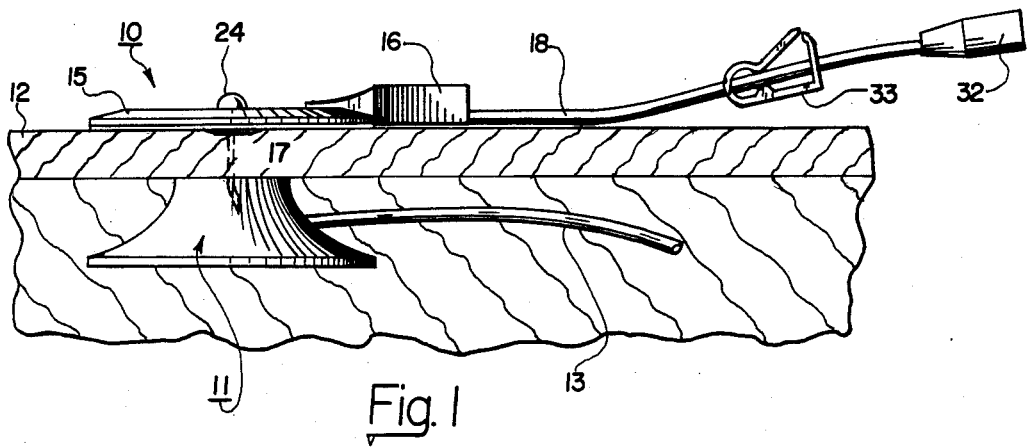
Fig. 1
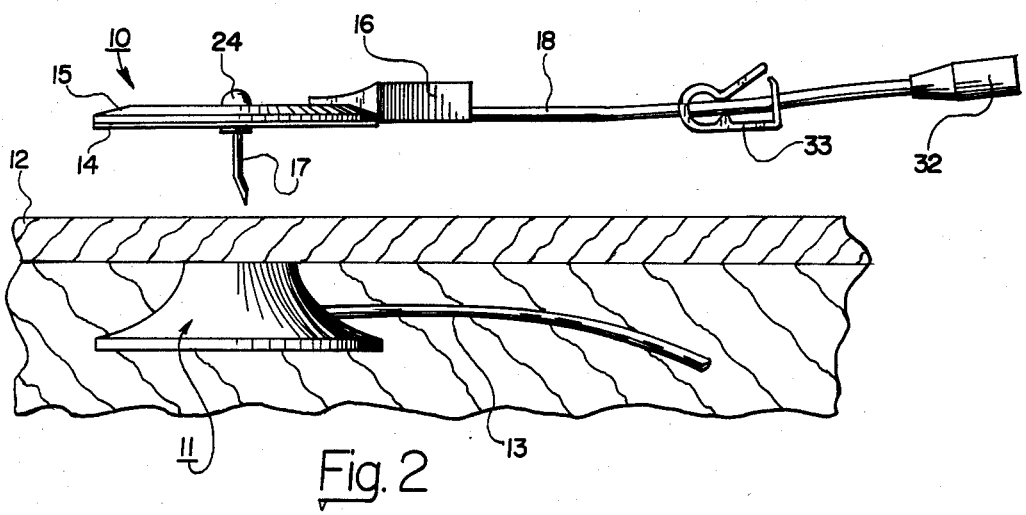
Fig. 2
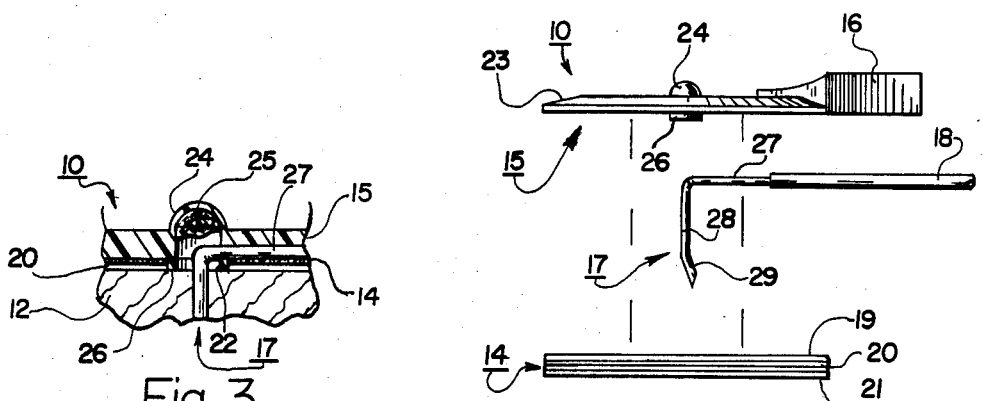
Fig. 3
Fig. 4

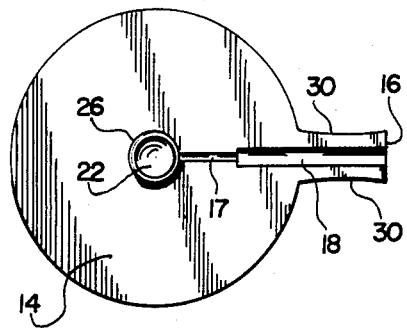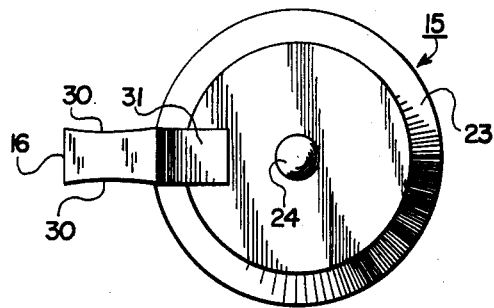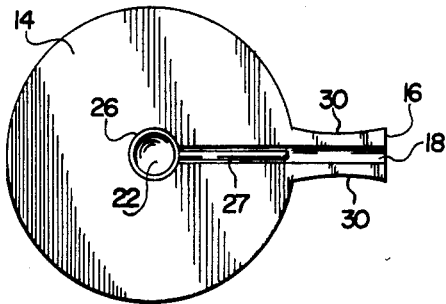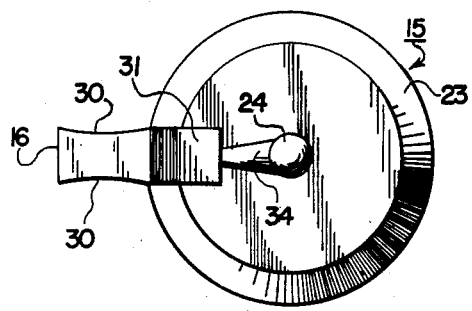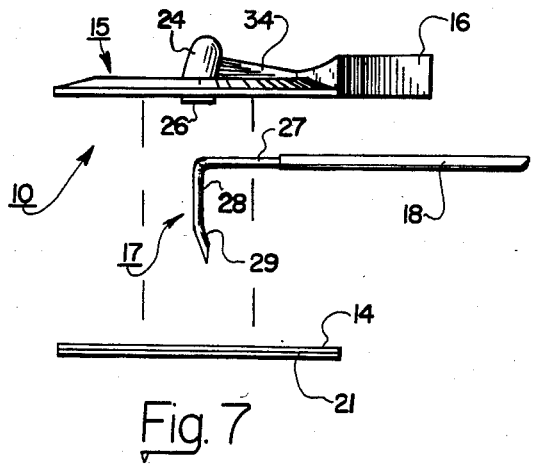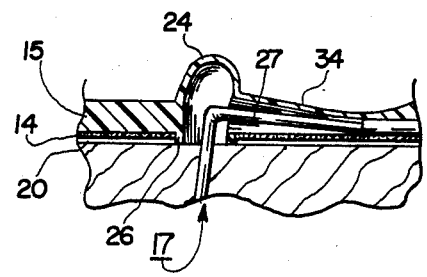

VASCULAR ACCESS IMPLANT NEEDLE PATCH

This invention relates to a vascular access implant needle patch.

In the past, it has been known to implant a vascular access device within the body of a patient in order to provide a convenient technique for administering drugs and fluids over a prolonged period of time. Generally, these devices include a self-sealing silicone septum encased in a port made of metal or plastic and attached to a silicone catheter. Usually, the catheter is placed in a vein for the delivery of a drug or fluid.

In order to enter the port of the vascular access device, use has been made of various types of devices, for example a Huber needle. Usually, the Huber needle is bent and deflected in order to prevent coring of the septum. In this resoect, regular hypodermic needles have not been used on the basis that such would damage the septum. In addition, a luer lock extension set has usually been provided with the Huber needle.

However, the techniques used for inserting a Huber needle have been rather cumbersome. For example, once the Huber needle has been inserted through the septum of a vascular access device, it has been necessary to use one piece of tape to support the needle and a second piece of tape to secure the luer lock extension. In addition, it has been necessary to apply an antiseptic, such as a povidone-iodine ointment, at the needle-to-skin junction. Still further, it has been necessarv to apply a dressing from a separate dressing kit to cover the injection site and to use a tape dressing to secure the gauze dressing.

Since the dressings have usually been made of opaque materials, it has been necessary to remove the dressings from time to time, for example every 24 or 48 hours, in order to inspect the injection site for possible sepsis.

Additional problems which are associated with the above procedure include the possibility of significant movement and "pistoning" of the Huber needle since the needle is not securely fixed in place at the injection site. Further, excessive antispetic ointment may be applied to the injection site with a result that there is a risk of a skin burn occurring. Still further, the insertion procedure requires the practitioner to use gloves since the practitioner's finger must push right up against the shank of the Huber needle.

Infusion needle attachments are also known, for example as described in U.S. Pat. No. 4,380,234, wherein an elastomeric member is attached to an infusion needle in order to conveniently handle and guide the needle into place. In particular, it has been known to provide a disc-like body with a tubular member at the periphery of the of the body and at a selected angular orientation in order to position a needle so that the presence of the needle can be masked by the disc-like body when implanted. However, such infusion needle attachments are generally not suitable for use with an implanted vascular access device.

Accordingly, it is an object of the invention to provide a simple needle patch which can be readily used with an implanted vascular access device.

It is another object of the invention to provide a needle patch which permits ready inspection of an injection site.

It is another object of the invention to deliver a controlled amount of antiseptic to an injection site.

It is another object of the invention to provide a needle patch which can be readily inserted into an implanted vascular access device.

It is another object of the invention to provide a needle patch which can be securely held in place on a patient after being inserted into an implanted vascular access device.

Briefly, the invention provides a needle patch which is comprised of a flexible patch for mounting on a patient, a rigid housing which is secured to the patch to define a finger grip and a hollow needle having an angled portion extending perpendicularly from the patch.

The flexible patch is made of transparent material and may include a pair of discs which are integrally secured together. In order to secure the patch in place, an adhesive layer may be formed on a lower surface of the oatch and may be covered over by a removable sheet which can be removed for application of the needle patch to a patient.

The needle is positioned between the discs of the patch so that the angled portion passes through a central aperture in one disc while a main portion of the needle is disposed between the two discs and extends into the rigid housing. In addition, a flexible tube is connected to the main portion of the needle within the rigid housing and may carry a luer connection at the opposite end.

The upper disc of the patch is also provided with a means to define a reservoir above the aperture in the lower disc for receiving an antiseptic, such as an antiseptic ointment. In addition, an annular wall may extend from the upper disc through the aperture in the lower disc in order to define a dam for retaining the antiseptic ointment.

In order to use the needle patch, the finger grip provided by the rigid housing is first grasped with the middle finger and thumb. Next, with the fore finger positioned over the needle, that is on the upper surface of the transparent patch, the releasable sheet is removed to expose the adhesive layer and the needle inserted into a septum of a vascular access device implant within a patient. With this technique, there is no need to touch the injection site or the needle. As such, a sterile insertion technique can be obtained without need for the practitioner to be gloved.

If an antispetic ointment has been placed in the reservoir prior to needle placement, the ointment may be expelled from the reservoir after insertion of the needle so as to deposit a small quantity of the ointment at the injection site. At this time, the dam prevents a migration of the ointment which might otherwise cause a lift-off between the adhesive layer and the skin of the patient.

Once the needle has been inserted, it is possible to inspect the injection site for contamination by viewing directly through the transparent discs. Thus, there is no need to remove the patch in order to evaluate the site.

Of note, the adhesive layer on the patch serves to securely fix the needle patch in place. The strength of this adhesive should be such that the lateral tugging of the tube attached to the patch causes the tube to "neck down" before the patch would separate from the skin of the patient. Further, the tube permits various types of drugs and fluids to be administered to a patient from a remote hook-up.position away from the injection site.

In another embodiment, the Huber needle may be formed with a main portion which extends at an angle to the lower disc of the needle patch. In this case, the upper disc would be provided with a cavity to receive the needle When such a needle is inserted into a vascular access device, a slight rotation of the needle occurs. In the case of a Huber needle, this facilitates entry of the tip of the needle through a septum. Further, since the upper disc is flexible, rotation of the needle can be readily accomplished.

These and other objects and advantages of the invention will become more apparent from the following detailed description taken in conjunction with the accompanying drawings wherein:

FIG. 1 illustrates a needle patch according to the invention mounted in place;

FIG. 2 illustrates the needle patch of FIG. 1 immediately prior to insertion into an implanted vascular access device;

FIG. 3 illustrates a partial cross sectional view of the needle patch of FIG. 1;

FIG. 4 illustrates an exploded view of the needle patch of FIG. 1;

FIG. 5 illustrates a bottom view of the needle patch of FIG. 1;

FIG. 6 illustrates a top view of the needle patch of FIG. 1;

FIG. 7 illustrates an exploded view of a modified needle patch according to the invention;

FIG. 8 illustrates a bottom view of the needle patch of FIG. 7;

FIG. 9 illustrates a top view of the needle patch of FIG. 7; and

FIG. 10 illustrates an enlarged view of the needle of the needle patch of FIG. 7.

Referring to FIG. 1, the needle patch 10 is constructed for use with a vascular access device 11 which is implanted under the skin 12 of a patent. In this respect, the vascular access device is of known construction and includes a catheter 13 for connection with a vein or artery of the patient.

Referring to FIGS. 2 and 4, the needle patch 10 includes a pair of flexible transparent discs 14, 15 which are integrally secured together so as to form a flexible patch for mounting on the patient. In addition, a rigid housing 16 is integrally molded to the upper disc 15 and is shaped to define a finger grip. Still further, a hollow needle 17, such as a Huber needle, is sandwiched between the discs 14, 15 and is connected to a flexible tube 18 which extends from the housing 16.

Referring to FIG. 4, the lower disc 14 is in the form of a carrier film which is provided on the topside with a layer of adhesive 19 in order to secure the carrier film to the upper disc 15. In addition, the carrier film is provided on the underside with a layer of adhesive 20 as well as with a removable sheet 21 which is disposed over the adhesive layer 20 in order to protect the adhesive. In addition, as indicated in FIG. 5, the lower disc 14 has a central aperture 22 for passage of the needle 17.

The upper disc 15 is of the same diametric size as the lower disc 14 and may be provided with a tapered rim 23 (see FIG. 6) to impart flexibility at the edge of the path 10 for securement to the skin 12. In addition, the upper disc 15 is provided with a means such as a dome-shaped projection 24 for defining a reservoir about the aperture 22 in the lower disc 14 in order to receive an antiseptic, such as an antiseptic ointment 25 (see FIG. 3). Still further, the upper disc 15 is provided with an annular wall 26 which extends from the disc 15 through the aperture 22 in the lower disc 14 in order to define a dam for retaining the ointment 25 which is expelled from the reservoir defined by the projection 24. This wall 26 is provided with a small slit (not shown) to accommodate passage of the passage of the needle 17 without leakage of ointment.

The needle 17 is secured to the flexible tube 18 via a suitable cement so as to form a fixed connection. In addition, the needle 17 has a main portion 27 which extends in parallel between the discs 14, 15 and a downwardly angled portion 28 which extends perpendicularly through the aperture 22 in the lower disc 14. As indicated in FIG. 4, the free end 29 of the needle 17 is slightly angled relative to the angled portion 28 as is known. By being connected to the housing 16, the hollow needle 17 rigidifies the housing 16 and provides a finger grip carrier to hold the needle 17 during septum puncture.

The housing 16 is integrally molded with the upper disc 15 to form a one piece construction. As indicated in FIG. 6, the side walls 30 of the housing 16 are slightly indented so as to provide a finger grip, for example for the thumb and middle finger. The transparency of the housing also permits a clear view of the needle 17 and tube 18. In this respect, the main portion 27 of the needle 17 extends substantially through the housing 17 while the tube is inserted a short distance into the housing.

The housing 16 is also provided with a shaped surface 31 located over the main portion of the needle 17 to provide a further finger grip, for example for the index finger.

Referring to FIG. 2, the tube 18 may have a luer connection 32 at the free end as well as a clamp 33 at an intermediate point.

In order to use the needle patch 10, the usual procedures would be followed in order to connect the luer connection 32 to an administration set and to clear the tube 18 and needle 17 of air. Thereafter, the needle patch 10 is grasped, for example by gripping the surfaces 30 between the thumb and middle finger. Next, the removable sheet 21 is stripped from the lower disc 14 and the needle 17 inserted through the skin 12 of the patient into and through a septum (see FIG. 1) in the implanted vascular access device 11. At this time, pressure can be applied by an index finger on the shaped surface 31 as well as on the upper disc 15 over the main portion 27 of the needle 17 in order to provide sufficient force to insert the angled portion 28 of the needle. Once inserted, the adhesive layer 20 on the underside of the bottom disc 14 securely fixes the needle patch 10 to the skin 12 of the patient (see FIG. 3). Thereafter, the projection 24 may be depressed manually so as to dispense the ointment 25 into the dam defined by the annular wall 26 at the injection site.

Because of the transparency of the discs 14, 15, the injection site can be readily viewed from time to time to check for sepsis. As a result, there is no need to remove the patch 10 from a patient nor is there any need to change any dressings from time to time.

Because adhesive layer 20 surrounds the injection site, the adjesive layer 20 serves as a barrier against contamination from the outside environment. Hence, the injection site can be kept clean.

As indicated in FIGS. 3 and 4, the lower disc 14 is of a smaller thickness than the upper disc 15. For example, the thickness of the lower disc may be 0.005 inches while the thickness of the upper disc 15 is 0.060 inches. The overall diameter of the discs 14, 15 may be about 1.750 inches.

The adhesive 20 should also be of such a nature as to form a relatively fixed connection between the oatch 10 and the skin 12 of the patient so that any lateral tugging of the tube 18 causes the tube 18 to neck down before the patch 10 separates from the skin 12.

Of note, the needle 17 contains a continuous passage for the flow of a fluid therethrough.

Referring to FIGS. 7 to 10, wherein like reference characters indicate like parts as above, the needle patch 10' may be constructed to accommodate different thicknesses of skin and different thicknesses of imolanted access devices. In this respect, it is known that the combined thickness of an implanted access device and the skin of a patient may vary significantly from patient to patient. Hence, the upper disc 15 is provided with an integral guide channel 34 to receive the main portion 27' of the needle 17. As indicated in FIG. 7, the main portion 27' of the needle 17 is initially horizontally disposed. Should the needle 17 bottom within an access device 11 prior to securement of the patch 10' to the skin of the patient, the needle 17 may pivot upwardly into a position as illustrated in FIG. 10. The guide channel 34 is thus able to accommodate the pivoting movement of the main needle portion 27'.

Of note, the guide channel 34 is disposed in spaced relation above the needle 17 so as to avoid restraining upward movement of the needle 17. In this respect, the total available travel for the needle may be just under one quarter inch.

Alternatively, the needle 17' may be initially formed with an upwardly angled needle portion with a depending portion 28' passing through the aperture 22 in the lower disc 14 at a slight angle from a perpendicular while the free end 29' is perpendicular to the plane of the disc 14. When put to use, the finger pressure exerted on the needle 17' for insertion causes the free end 29' of the needle 17 to first pierce the skin and the underlying septum (not shown) of a vascular access device with a slight pivoting or rotation movement.

While the transparent discs 14, 15 have been described as being flexible, these discs may also be made of a relatively rigid material where such can be applied to the skin of a patient.

The invention thus provides a needle patch which can be conveniently inserted into a vascular access device implanted in a patient.

Further, the needle patch can be manufactured of relatively simple materials in a relatively simple and inexpensive manner.

Further, the invention provides a needle patch which permits viewing of the injection site and which does not require frequent changes of dressings.

What is claimed is:

1. A vascular access implant needle patch comprising
    a first transparent disc having a centrally disposed aperture;
    a needle having a passage for a flow of fluid therethrough, said needle having a main portion extending over said disc and an angled portion extending through said aperture of said disc;
    a second transparent disc secured to said first disc with said needle disposed therebetween; and
    a rigid housing secured to said discs to define a finger grip, said housing having said main portion of said needle encased therein.

2. A needle patch as set forth in claim 1 which further comprises an adhesive layer on said first disc and a removable sheet disposed over said layer on said first disc.

3. A needle patch as set forth in claim 1 wherein said main portion of said needle extends parallel to said first disc.

4. A needle patch as set forth in claim 1 wherein said main portion of said needle extends at an angle to said first disc.

5. A needle patch as set forth in claim 1 wherein said second disc includes a dome-shaped projection over said aperture in said first disc to define a reservoir for receiving an antiseptic ointment.

6. A needle patch as set forth in claim 5 which further comprises an annular wall extending from said second disc through said aperture in said first disc to define a dam for retaining ointment from said reservoir therein.

7. A needle patch as set forth in claim 1 which further comprises a flexible tube connected to said needle within said housing and extending from said housing.

8. A needle patch comprising
    a transparent patch for mounting on a patient, said patch including a centrally disposed aperture and means defining a reservoir above said aperture for receiving an antiseptic ointment;
    a rigid housing secured to said patch to define a finger grip; and
    a hollow needle having an angled portion extending through said aperture of said patch and perpendicularly from said patch.

9. A needle patch as set forth in claim 8 which further comprises an adhesive layer on said patch for adhering said patch to a patient.

10. A needle patch as set forth in claim 8 wherein said angled portion of said needle is disposed centrally of said patch.

11. A needle patch as set forth in claim 10 wherein said needle has a main portion extending into said housing and which further comprises a flexible tube connected to said main portion of said needle.

12. A needle patch as set forth in claim 8 further comprising an adhesive layer on said patch for securing said patch to a patient and a removable sheet disposed over said adhesive layer to protect said layer.

13. A needle patch as set forth in claim 8 wherein said patch is flexible.

14. A needle patch as set forth in claim 13 wherein said patch includes a pair of discs integrally secured together and said needle includes a main portion extending between said discs.

15. A vascular access implant needle patch comprising
    a flexible transparent disc for mounting on a patient;
    a second disc secured to said flexible disc;
    a rigid housing secured to and extending radially of said second disc to define a finger grip;
    a hollow needle having a main portion extending between said discs into said housing and an angled portion extending perpendicularly from a central portion of said flexible disc;
    a layer of adhesive on said flexible disc for securing said flexible disc to a patient; and
    a removable sheet disposed over said adhesive layer.

16. An implant needle as set forth in claim 15 wherein said second disc includes a dome-shaped projection over said angled portion of said needle to define a reservoir for an antiseptic and said flexible disc includes an aperture aligned with said projection with said angled portion of said needle passing therethrough.

17. An implant needle as set forth in claim 15 wherein said disc has an integral guide channel receiving said main portion of said needle in spaced relation to permit pivoting of said main portion within said channel.

18. A vascular access implant needle patch comprising
- a first transparent disc having a centrally disposed aperture;
- a needle having a passage for a flow of fluid therethrough, said needle having a main portion extending over said disc and an angled portion extending through said aperture of said disc; and
- a second transparent disc secured to said first disc with said needle disposed therebetween, said second disc including a dome-shaped projection over said aperture in said first disc to define a reservoir for receiving an antiseptic ointment.

19. A needle patch as set forth in claim 18 which further comprises an annular wall extending from said second disc through said aperture in said first disc to define a dam for retaining ointment from said reservoir therein.

20. A needle patch as set forth in claim 18 which further comprises a rigid housing secured to said discs to define a finger grip, said housing having said main portion of said needle encased therein.

21. A vascular access implant needle patch comprising a flexible transparent disc for mounting on a patient;
- a rigid housing secured to and extending radially of said disc to define a finger grip;
- a hollow needle having a main portion extending into said housing and an angled portion extending perpendicularly from a central portion of said disc;
- an integral guide channel in said disc receiving said main portion of said needle in spaced relation to permit pivoting of said main portion within said channel;
- a layer of adhesive on said disc for securing said disc to a patient; and
- a removable sheet disposed over said adhesive layer.

* * * * *

UNITED STATES PATENT AND TRADEMARK OFFICE
CERTIFICATE OF CORRECTION

PATENT NO. : 4,645,495

DATED : February 24, 1987

INVENTOR(S) : Vincent L. Vaillancourt

It is certified that error appears in the above—identified patent and that said Letters Patent is hereby corrected as shown below:

Column 1, line 18 "resoect" should be -respect-
Column 1, line 30 "necessarv" should be -necessary-
Column 1, line 55 "of the of the body" should be -of the body-
Column 2, line 17 "oatch" should be -patch-
Column 4, line 2 "passage of the passage of" should be -passage of-
Column 5, line 2 "oatch" should be -patch-
Column 5, line 11 "imolanted" should be -implanted- Signed and Sealed this Twenty-seventh Day of October, 1987

Attest:

DONALD J. QUIGG

Attesting Officer

Commissioner of Patents and Trademarks